United States Patent [19]

Tregear et al.

[11] Patent Number: 4,656,249

[45] Date of Patent: Apr. 7, 1987

[54] PEPTIDES WITH RELAXIN ACTIVITY

[75] Inventors: Geoffrey W. Tregear, Hawthorn, Australia; Yu-cang Du, Shanghai, China; Hugh D. Niall, Elwood, Australia

[73] Assignee: Howard Florey Institute of Experimental Physiology and Medicine, Melbourne, Australia

[21] Appl. No.: 387,131

[22] Filed: Jun. 10, 1982

[51] Int. Cl.$^4$ .................................................. C07K 7/10
[52] U.S. Cl. ..................................... 530/324; 530/325
[58] Field of Search ...................... 260/112.7; 530/324, 530/325

[56] References Cited

U.S. PATENT DOCUMENTS 3,420,810  1/1969  Katsoyannis et al. ........... 260/112.7
4,421,685 12/1983  Chance et al. .................... 260/112.7
4,423,037 12/1983  Rosenblatt et al. .................... 514/12

OTHER PUBLICATIONS

Chem. Abstr. vol. 97, (1982) 72749.
Chem. Abstr. vol. 97, (1982) 72751.
Dixon, Symposium 58, pp. 1207-1215 "Recombination of Insulin A & B Chains, Hybrid Insulins & Synthetic Insulin.
Dixon, Biochimica et Biophysica Acta (1962) 483-489.
Katsoyannis, Diabetes 13, Jul. & Aug. (1961) 339, 348.
Scientia Sinica, 10, 84-104 (1961); 14, 229-236 (1965), 15, 544-561 (1966).
Dixon, et al, Nature, Nov. 26, 1960, 721-724.
Kexue Tongbao, (Republic of China) 17, 241-277, (1966).
Science, 154, 1509-1514, (1966), Katsoyannis.
Nature, vol. 267, 1977, pp. 544-546.
Biochem. and Biophys. Res. Commun. 74, 1977, pp. 1501-1504.
Biochem. and Biophys. Res. Commun. 70, 1976, 397-405.
FEBS Letters, 1981, vol. 129, No. 1, pp. 80-82.

*Primary Examiner*—Delbert R. Phillips
*Attorney, Agent, or Firm*—Sughrue, Mion, Zinn, Macpeak & Seas

[57] ABSTRACT

A method for the synthesis of porcine relaxin or modified forms or analogues thereof, which comprises the steps of reducing a mixed solution of the S-sulfonated A and B peptide chains, or modified forms or analogues thereof; precipitating the reduced peptides with acetone; washing the mixed peptides; oxidizing the mixed peptides in the presence of aqueous sodium chloride; and isolating the relaxin thus produced.

Also claimed are modified forms and analogues of porcine relaxin analogues which comprise shortened forms of the natural B and/or A peptide chains, and/or in which one or both of A and B chains in the full length or shortened form has been chemically modified.

23 Claims, 11 Drawing Figures

FIG. 1

A CHAIN

H − ARG − MET − THR − LEU − SER − GLU − LYS − CYS − GLN − VAL − GLY − CYS
1                                   5                                    10

ILE − ARG − LYS − ASP − ILE − ALA − ARG − LEU − CYS − OH
                15                           20        22

B CHAIN

PCA − SER − THR − ASN − ASP − PHE − ILE − LYS − ALA − CYS − GLY − ARG − GLU
1                                  5                                    10

LEU − VAL − ARG − LEU − TRP − VAL − GLU − ILE − CYS − GLY − SER − VAL − SER
                15                           20                          25

TRP − GLY − ARG − THR − ALA − OH
      28    29    31

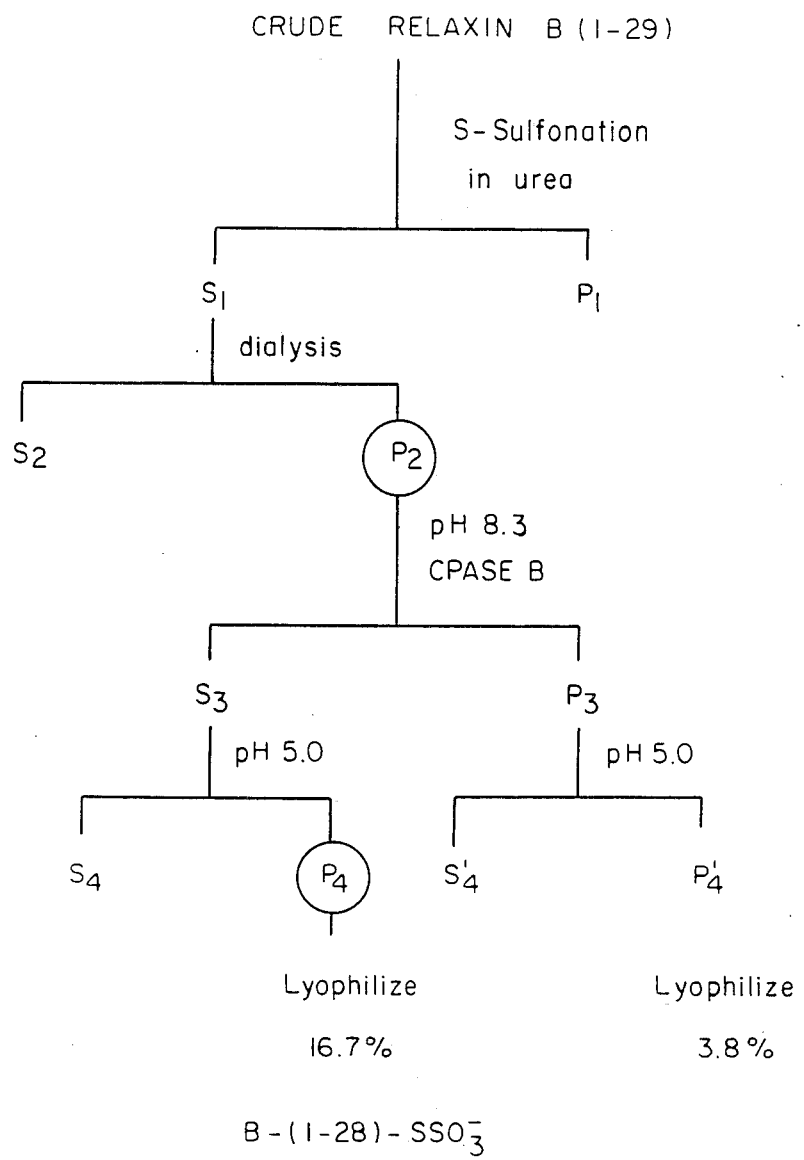

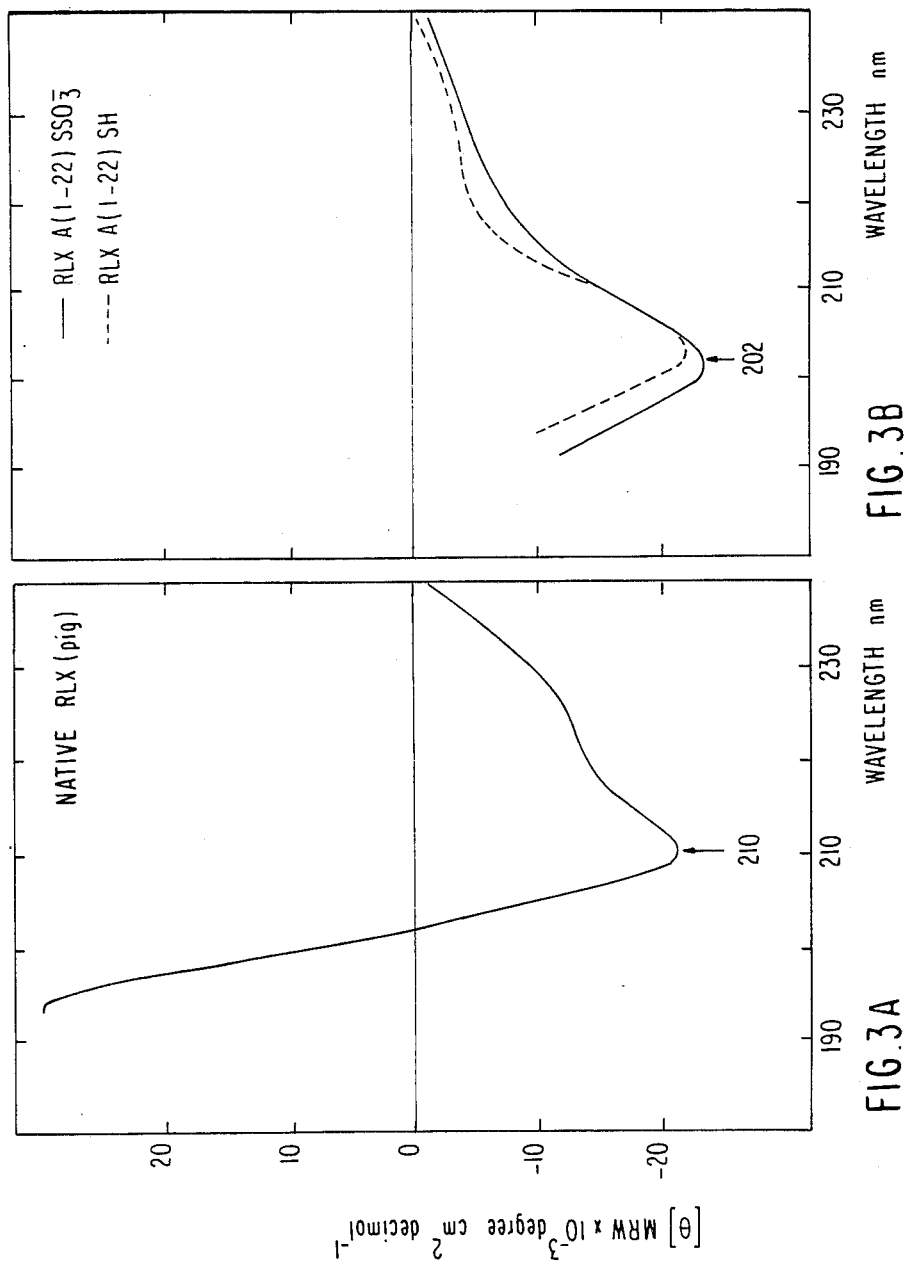

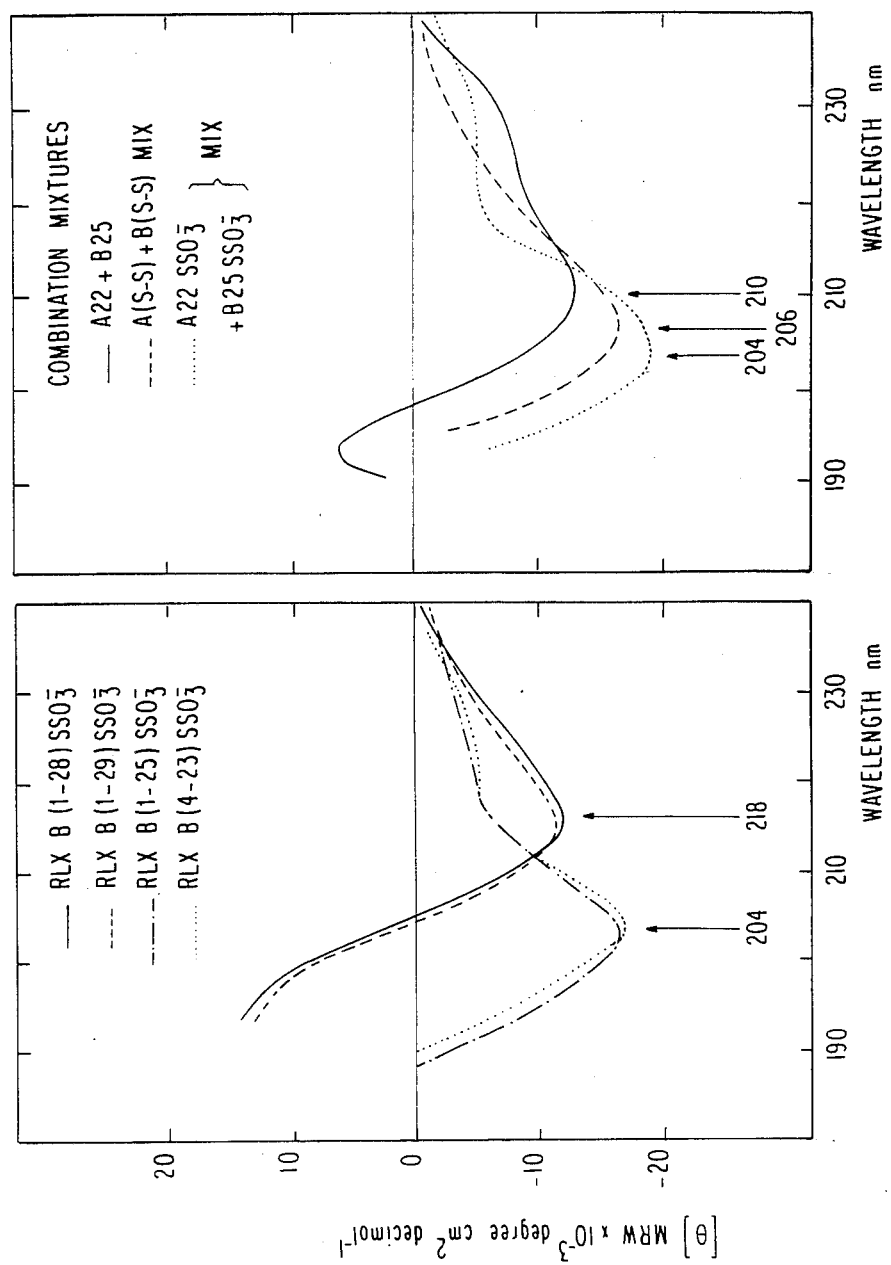

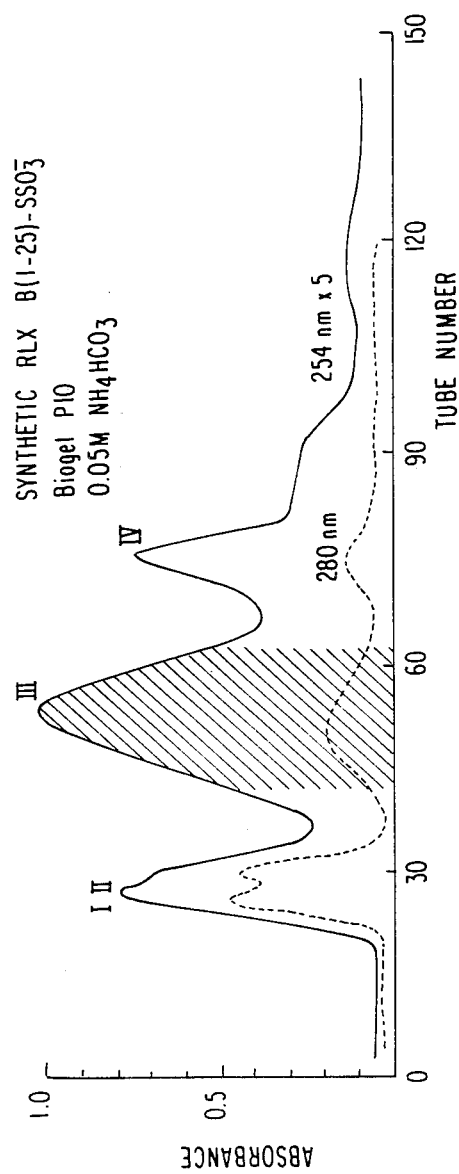
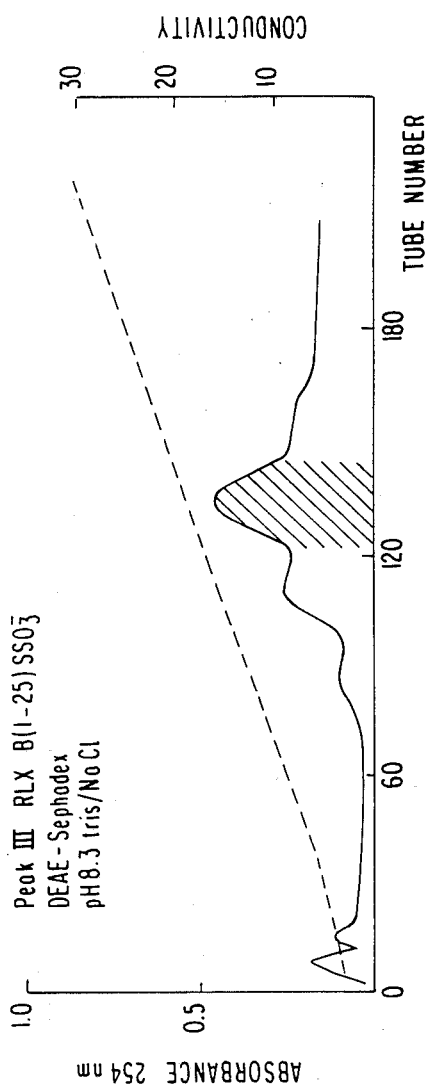
FIG. 4B
FIG. 4C

PEPTIDES WITH RELAXIN ACTIVITY

This invention was made with government support under Grant No. HD11908 awarded by the Department of Health and Human Services, Public Health Service, Office of Grants and Contracts, National Institute of Child Health and Human Development. The Government has certain rights in this invention.

This invention relates to the synthesis of peptides with relaxin activity. The invention is particularly concerned with the synthesis of porcine relaxin and some structural analogues.

FIELD OF THE INVENTION

The ovarian peptide hormone relaxin plays an important role in pregnancy and parturition. The main biological action of the hormone is to soften and lengthen the inter-pubic ligaments: it also dilates the cervix and inhibits contractions of the uterus.

DESCRIPTION OF THE PRIOR ART

Relevant prior art is contained in the reference cited herein which are identified by numbers in brackets in the text and are collected together at the end of this description. Other prior art is collected and described in the specification of British Pat. No. 2,072,680 (equivalent to U.S. Ser. No. 134,390, filed Mar. 27, 1980). The content of these references is hereby incorporated into this specification.

The complete amino acid sequence of relaxin extracted from the ovaries of the pregnant pig has been recently established (5, 6) and is shown in FIG. 1 of the accompanying drawings. The amino acid sequence of rat relaxin has also been elucidated (7, 8) and Gowan et al. (9) have reported a partial sequence analysis of the hormone from the shark ovary.

The general structural features of the relaxin molecule bear striking resemblance to insulin. Relaxin is composed of two peptide chains (A and B) joined by disulfide bonds through the cysteines at A9 B10 and A22-B22 (see FIG. 1), with an intra-chain disulfide bridge within the A-chain between A8 and A13. The disposition of the disulfide bonds is thus analogous to that of insulin. A model of the relaxin sequence can be accommodated without strain into the three-dimensional coordinates of the insulin structure (10, 11) and circular dichroism analyses of the hormones in solution are very similar (12, 13). Thus relaxin and insulin may share common features of secondary and tertiary structure even though the hormones have no measurable overlap in biological or immunological properties (13).

Three forms of relaxin of equivalent biological activity, which are characterized by their elution behaviour on carboxymethyl cellulose chromatography, have been isolated from the ovaries of the pregnant pig. These forms of relaxin have been designated CMB, CMa' and CMa by Sherwood & O'Bryne (14). Sequence analysis has revealed that these three forms of pig relaxin have an identical A chain of 22 amino acids but differ in sequence at the carboxyl terminus of the B chain (16). CMa relaxin has a B-chain of 31 amino acids; the B-chains of CMa' and CMB are shorter, having 29 and 28 residues respectively (see FIG. 1).

The predominant form of the hormone stored in the pig ovary is the CMa or B31 variant: the CMB and CMa' peptides are probably largely generated during the isolation procedures (15).

We have carried out research into the chemical synthesis of relaxin and its structural analogues as part of a systematic study of the structure-function relationships in the hormone molecule. The purified separate chains of pig relaxin have been obtained in approximately 10% yield (based on crude). The major impurities in the synthetic peptides appear to have arisen through side-reactions of the cysteine residues occurring during the HF cleavage step. In more recent syntheses improved yields have been obtained using the HF stable S-ethyl mercapto protecting group for cysteine. We have found that both the natural and synthetic B chains of pig relaxin, whether in the reduced or S-sulfonated form, are particularly difficult to dissolve in aqueous solution. In addition, the relaxin B chains exhibit unusual adsorptive properties. Column chromatography on Sephadex, cellulose, polyamide or polystyrene resins results in virtually a complete loss of peptide by irreversible absorption (16). These properties have made purification of synthetic relaxin B chain peptides and their coupling to A chain particularly difficult. Detailed studies of the conformation of the relaxin B chains by circular dichroism have revealed that the configuration of the B31, B29 and B28 peptides in solution were largely beta-structure.

We have found that conditions which give efficient combination of the insulin A and B chains (17) give very low or negligible yields when use for the structurally related relaxin. Our investigations have now shown that precipitation of the mixed relaxin peptide chains with acetone, to remove reducing agent, and the addition of 0.5 M NaCl during the oxidation (recombination) step are essential requirements.

It is an object of the present invention to provide methods for the preparation of porcine relaxin and its structural analogues which provide improved product yields over the known art.

More specifically, one object of the invention is to provide a method for joining the A and B chain peptides of natural and/or synthetic porcine relaxin.

Another object is to provide a method of producing relaxin analogues by combining modified forms of the natural B and/or A relaxin chains.

A further object is to provide modifications and/or structural analogues of natural porcine relaxin.

Other aims and objects of the invention will be apparent from the following description.

SUMMARY OF THE INVENTION

In accordance with one aspect of the present invention, there is provided a method for the synthesis of porcine relaxin which comprises the steps of reducing a mixed solution of the S-sulfonated A and B peptide chains; precipitating the reduced peptides with acetone; washing the mixed peptides; oxidizing the mixed peptides in the presence of aqueous sodium chloride; and isolating the relaxin thus produced.

More specifically in accordance with this aspect of the invention, a method for the synthesis of porcine relaxin comprises the steps of:
- separately preparing or isolating the S-sulfonated A and B peptide chains;
- forming a mixture of the S-sulfonated A and B peptides;
- reducing the mixture at pH 7 to 9, preferably 8.3, under nitrogen for at least 6 minutes;
- adjusting the pH of the reduced mixture to 4.5 to 5.5, preferably pH5, with acetic acid;

adding acetone to the mixture to precipitate the mixed peptides;

washing the mixed peptides with a suitable solvent, preferably ethyl acetate and ether, to remove the reducing agent;

oxidizing the mixed peptides at pH 9.5 to 11, optimally at about 10.4 to 10.6, for about 48 to 72 hours at about 0° to 10° C., preferably 5° C., in the presence of sodium chloride, in a concentration of at least about 0.1 M, preferably about 0.5 to 1M.

Preferably, the isolation and purification of the product is carried using chromatographic methods.

BRIEF DESCRIPTION OF THE DRAWINGS

Throughout this specification reference will be made to the accompanying drawings in which:

FIG. 1 shows the amino-acid sequences of the A and B chains of porcine relaxin;

FIG. 2 shows diagrammatically, a purification procedure for a crude synthetic S-sulfonated relaxin B-chain;

FIG. 3 shows circular dichroism (CD) spectra for:
(a) native porcine relaxin;
(b) the S-sulfonated, and reduced (un-sulfonated) A chains;
(c) S-sulfonated, full-length and shortened B chains;
(d) combinations and mixtures of various A and B chains;

FIGS. 4a–4d show the results of typical purification procedures as described herein.

DETAILED DESCRIPTION OF THE INVENTION

Figure 4A:
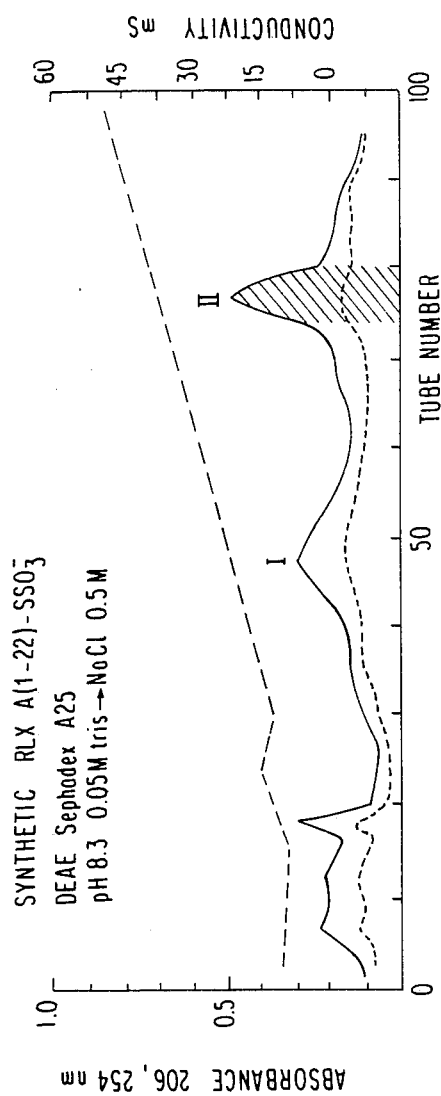

Using the above-described method, the natural A(1-22) and B(1-28) chains were combined in yields of up to 25% (based on the B chain). The combination yield for synthetic A(1-22) and B(1-28) chains was 0.7%.

We have also found that the combination yields of the synthetic A and B chains can be improved by shortening of the B chain at the carboxyl terminus to as little as 25 residues. As shown by FIG. 3(c), the CD spectra indicate that shortening to 25 residues results in a change of from the beta-configuration to an unordered conformation. This conformational change is reflected in an enhanced solubility of the peptide in aqueous solution, a loss of the adsorptive behaviour and an improvement in the combination yield with the A chain. Using the above-described method the combination yield rises to 10%. The specific activity of the A22 B25 peptide as so prepared is 33% of that of the natural A22 B31 peptide. After purification, the A22 B25 peptide has a specific activity of 93% of the native A22 B31 relaxin. As shown in FIG. 3(d) the CD spectrum of the A22 B25 peptide closely resembles that of native relaxin (FIG. 3(a)).

Shortening is also tolerated at the amino terminus of both the A and B chains as well as at the carboxyl terminus of the B chain. The B(4-23)NH₂ chain has a similar CD spectrum (FIG. 3(c) to the B(1-25) chain. The synthetic peptide A(4-22)B(4-23)NH₂ still retains significant biological activity.

Thus in accordance with another aspect of this invention, there is provided a porcine relaxin analogue consisting essentially of shortened forms of the natural B and/or A peptide chains.

This aspect of the invention also provides a method for producing a porcine relaxin analogue which comprises the step of forming the shortened B and/or A peptide chains and combining them by the method of the invention as described above.

The preferred shortened chain combinations are A(1-22) and B(1-25).

A further aspect of the present invention provides for chemical modification of the B and/or A chains (in either full-length or shortened form) prior to combination by the method of the invention. Two types of chemical modification may be employed, either singly or in combination.

The first type involves the modification of one or more of the amino-acids which occur in the natural B and/or A chains. Such modification will generally involve protection of active groups on one or more of the amino-acids by methods known per se, and the protecting groups may, if desired, be removed after combination of the (modified) A and B chains.

Examples of this type of modification include the acetylation or similar protection of free amino groups, amidation of C-terminal groups, or the formation of esters of hydroxyl or carboxylic groups. The formyl group is a typical example of a readily-removable protecting group.

The second type of modification includes replacement of one or more of the natural amino-acids in the B and/or A chains with a different amino acid (including the D-form of a natural amino-acid). This general type of modification may also involve the deletion of a natural amino-acid from the chain or the addition of one or more extra amino-acids to the chain.

The purpose of such modifications is to enhance the combination yields of the A and B chains, while maintaining the activity of the product, i.e., relaxin or an analogue thereof, or to enhance the activity of the product for a given combination yield.

A specific example of the first type of modification is acetylation of the N-terminal amino group of the B chain (B28, B25 or B23) or the modification of a tryptophan residue by addition of a formyl group.

Examples of the second type of modification are (i) replacement of the Trp moiety at B27 with glycine (Gly), (ii) replacement of the Pca moiety at B1 with glutamine (Gln) or glutamic (Glu) and (iii) replacement of Met moiety at A2 with norleucine (Nle).

An example showing both types of modification is replacement of the Pca moiety at B1 with N-acetyl-glutamine.

The invention in this aspect also includes relaxin analogues formed from natural or shortened B and/or A chains modified in accordance with the invention as described above.

The invention, in its various aspects, is further described and elucidated in the following examples.

EXAMPLE 1

(a) Starting Materials

The three structural variants of native relaxin (A22B28, A22B29 and A22B31) were isolated from pregnant pig ovaries and purified according to the procedure described by Sherwood and O'Byrne (14). Purified A22B31 peptide was also prepared by the method of Walsh and Niall (15).

(b) Separation of insulin and relaxin chains by S. sulfonation.

The A and B chains of porcine insulin were separated by S-sulfonation and purified according to the procedure previously described (17). For the S. sulfonation and separation of relaxin chains, the following modification to this procedure was used. Native porcine relaxin (A22B29, 19.8 mg) was dissolved in 4 ml tris buffer (0.05 M, pH 8.3). To this solution was added sodium sulfite (28 mg) and sodium tetrathionate (14 mg) and the mixture stirred at 37° C. After 3.5 hours further sodium sulfite (14 mg) and sodium tetrathionate (7 mg) were added and the mixture stirred at 37° C. for an additional 3 hours and then left to stand at room temperature overnight. The precipitated B-chain S-sulfonate was separated from A. chain S-sulfonate by centrifugation at 3000 rpm for 10 minutes. The B-chain sulfonate was partially purified by dissolving in dilute ammonia solution (5 ml) and precipitating at pH5 by the addition of glacial acetic acid, followed by centrifugation. This procedure was repeated twice. The precipitate was then redissolved in dilute ammonia solution and lyophilized to yeild 11 mg of B29 S-sulfonate. The supernatant solutions obtained from the above procedure were combined and dialyzed for 2 days against distilled water and then lyophilized to yield 6.3 mg of S-sulfonated A-chain.

The above procedure was also used to separate the A and B chains of porcine relaxin A22B28 and A22B31.

The time course of S-sulfonation for relaxin and insulin peptides was followed by titration with p-chloromercuriobenzoic acid using procedures previously described (23).

When required, the S-sulfonated relaxin A-chain was further purified by ion exchange chromatography on DEAE-Sephadex A25 in tris-HCl buffer pH 8.5 using a sodium chloride gradient from 0 to 0.5 M. Attempts to purify S-sulfonated relaxin B-chain by ion-exchange chromatography generally resulted in a complete loss of peptide by adsorption to the column. A reasonably satisfactory purification of B-chain was achieved by dissolving the S-sulfonated mixture in 8 M urea formic acid pH 3.0 and applying the sample to a Dowex 5DWX2 ion-exchange column and eluting with a step-wise sodium chloride/urea gradient. Under normal conditions one would expect the S-sulfonated B-chain to elute first from the column. In practice, the B-chain adsorbed strongly to the Dowex and allowed the S-sulfonated A-chain to be eluted first. Purified S-sulfonated B-chain could be recovered, although in poor yield, by stripping the column with dilute ammonia solution at pH 9.5. Following dialysis and a precipitation-washing cycle at pH 9 and pH 3.8, S-sulfonated B-chain was obtained free from A-chain and sodium sulfite.

The S-sulfonated chains of relaxin were characterized by electrophoresis on cellulose acetate paper in phosphate buffer pH 7.8 (2000 V. for 20 minutes). The peptide spots were visualized by oxidation.

EXAMPLE 2

Synthesis of Porcine Relaxin A Chain

Figure 4D:
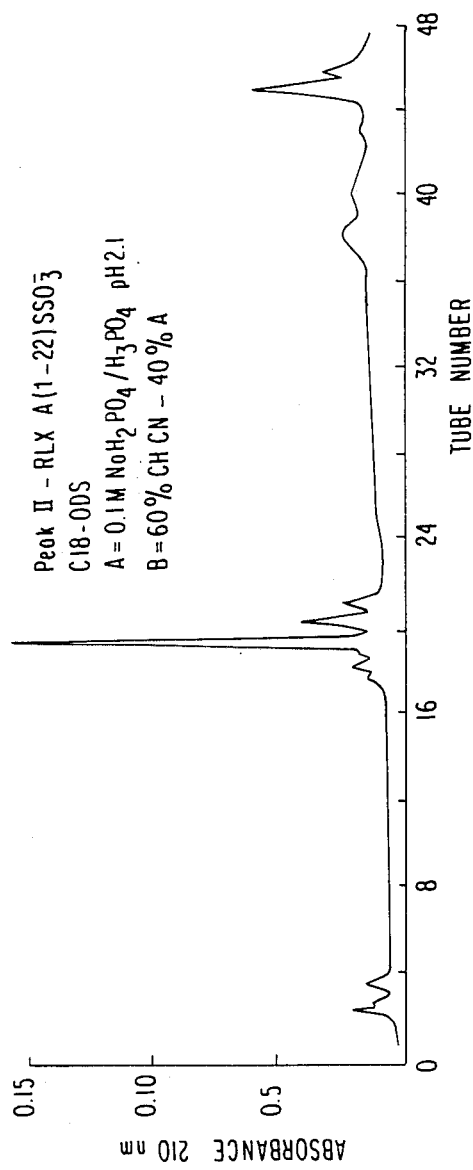
Figure 5:
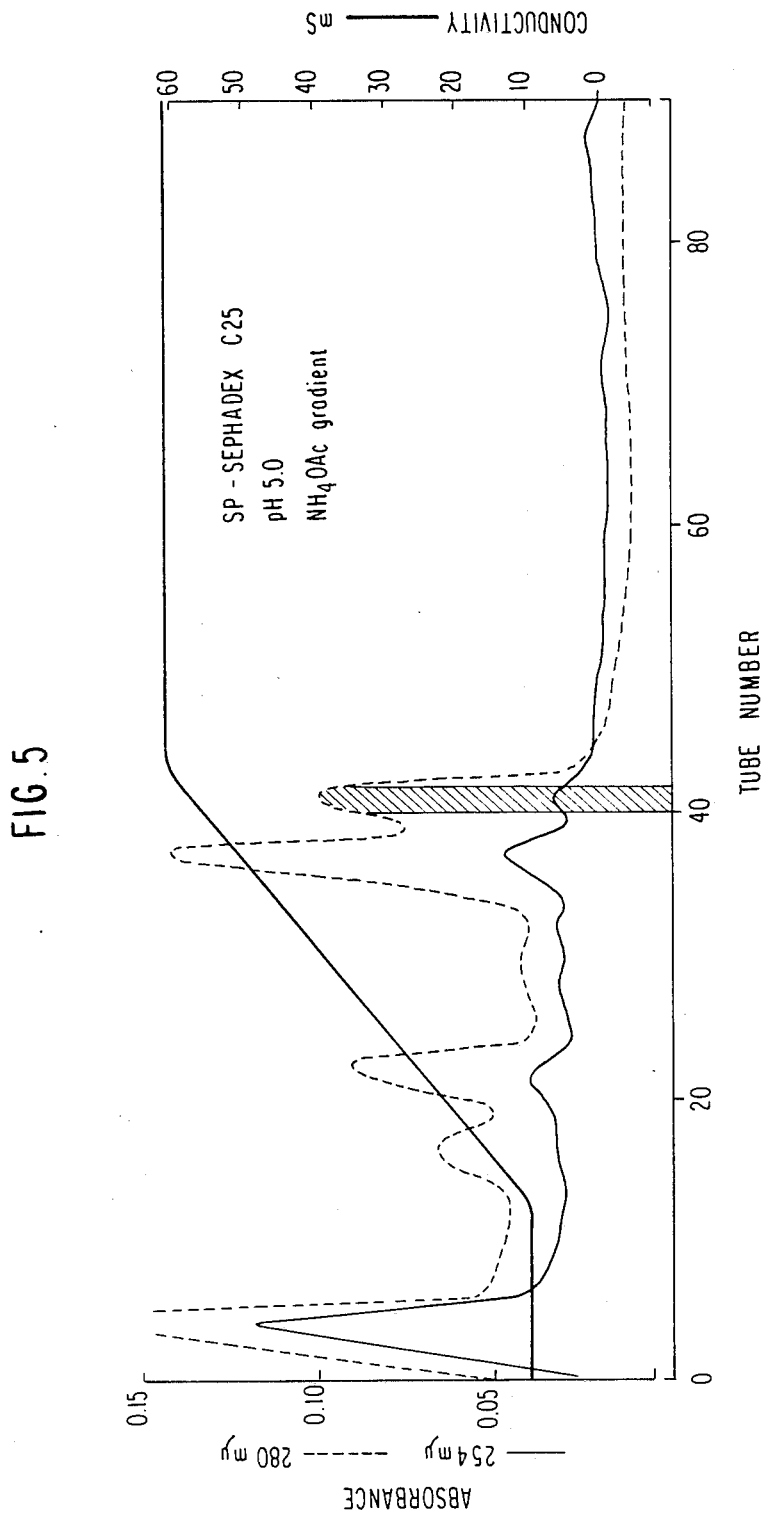
FIG. 5 shows the results for the final ion-exchange purification stage of a synthetic (A22 B25) combination mixture.

The 22-peptide chain representing the sequence of porcine relaxin A chain was assembled on a phenylacetamidomethyl - 1% cross linked polystyrene resin support (22) using standard solid-phase procedures (16). The amino acid side-chain functional groups were protected as follows: serine and threonine as the 0-benzyl ether, aspartic and glutamic acids as the benzyl ester, arginine as the p-toluenesulfonyl-, lysine as the 2-chlorocarbobenzoxy- and cysteine as the p-methoxybenzyl-derivatives respectively. The completed peptide was cleaved from the resin support with hydrogen fluoride in the presence of anisole (10%) for 30 minutes at 0° C. Exposure of the peptide to hydrogen fluoride was minimized to prevent formation of the glutamic acid anisole adduct. The crude peptide was reduced with dithiothreitol in 6 M guanidine hydrochloride and applied to a BioGel P10 column in 30% acetic acid. Further purification was by ion-exchange chromatography on SP-Sephadex with a pyridine-acetic acid gradient pH 2.5 to pH 5.0. The major peak from the SP-Sephadex column was S-Sulfonated (20) and applied to DEAE-Sephadex. The S-Sulfonated peptides were eluded with a linear gradient of NaCl to 0.5 M in tris-buffer (0.05 M), pH 8.3 (FIG. 4(a)). Relaxin A (1-22) $SSO_3^-$ eluted at a conductivity of 11 to 13 mS and was characterized following dialysis by amino acid analysis, HPLC (see FIG. 4(d)) and paper electrophoresis. The overall yield of purified Relaxin A (1-22) $SSO_3^-$ was generally of the order of 10% based on the initial amount of crude peptide.

EXAMPLE 3

Synthesis of Relaxin A Chain Analogue

In a separate synthesis, using the general procedures described in Example 2, an analogue of the relaxin A-chain was prepared wherein the methionine at position 2 was replaced with the isosteric norleucine residue.

EXAMPLE 4

Synthesis of Porcine Relaxin B-Chain

Initially, the synthesis of CMa' or B(1-29) was attempted using the same general strategy outlined for the A-chain synthesis in Example 2. The crude B(1-29) peptide exhibited unusual solubility characteristics. Although the crude peptide dissolved completely in dithiothreitol-guanidine-30% acetic acid, the vast majority of the peptide was lost by adsorption or precipitation following gel filtration on BioGel or Sephadex. The B-chain peptide was soluble above pH 5.5 but precipitated out of solution on ion-exchange columns when eluted with a salt gradient. The salting-out or adsorptive effect of the synthetic B-chain occurred whether the peptide was in the reduced or S-Sulfonated form and severely hampered attempts to purify the peptide by conventional chromatography. Adequate purification of the synthetic B-chain could only be effected by precipitating the peptide at pH 5 and washing away the soluble impurities. A marked improvement in the solubility of the relaxin B-chain was noted when the B(1-29) peptide (CMa') was converted to B(1-28) (CMB) by removal of the carboxyl terminal arginine residue with Cpase B. The purification scheme used for the synthetic S-Sulfonated relaxin B-chain, which resulted in a 15–20% yield based on the initial crude peptide, is outlined in FIG. 2.

A convenient method for monitoring the purification of the synthetic relaxin A and B chains was found to be paper electrophoresis on cellulose acetate in phosphate buffer at pH 7.8.

EXAMPLE 5

Synthesis of Relaxin B Chain Analogues

The B chain analogues set out in Table 1 below were prepared using the general procedures described in Example 2. FIGS. 4(b) and 4(c) show the results obtained in the first and final purification stages respectively for the synthetic S-sulfonated B(1-25) chain.

EXAMPLE 6

(a) The recombination reaction

Initially the S-sulfonated relaxin A and B chains were recombined using conditions previously formed to be optimal for the recombination of insulin chains (24). As the recombination yields obtained for relaxin were low using this general procedure (of the order of 1 to 2%), we investigated the solubility characteristics of the relaxin A and B chains, the influence of chain length of the relaxin B chain, the effect of the addition of urea, sodium chloride or dioxam to the recombination mixture, the ratio of A and B chains and the time of oxidation. The conformation of the relaxin A and B chains in solution and the structural changes occurring during chain combination were followed by circular dichroism spectroscopy (25).

(b) Preferred conditions for the recombination of porcine Relaxin A and B chains S. sulfonated relaxin A chain (1.0 mg) and S.sulfonated relaxin B chain (1.0 mg) were dissolved in 0.05 M tris-HCl buffer pH 8.3 (0.2 ml) in a stoppered test tube and the solution cooled to 0° C. in an ice bath. A solution of mercaptoethanol in water (1.4 N) was adjusted to pH8 by the dropwise addition of dilute ammonia solution and 0.12 ml added to the solution of relaxin chains. The mixture was agitated and degassed three times with oxygen free nitrogen and placed in a 37° C. water bath for 5.5 minutes. The solution was then adjusted to pH 4.5 with 30% acetic acid and the peptide chains precipitated by the addition of acetone (4 ml). The mixture was cooled to 0° C. for 5 minutes then centrifuged. The precipitate was then wasted further with acetone (4 ml), ethyl acetate (4 ml) and finally petroleum ether (4 ml) and dried in vacuo. The precipitate was then dissolved in degassed water (0.2 ml) previously brought to pH 10 with the addition of 0.5 N sodium hydroxide. To this solution was added 0.05 M glycine buffer pH 10.6 (0.4 ml) and sodium chloride to give a final concentration of 1 M and the mixture agitated and allowed to stand for 3 days at 4° C. The reaction mixture was centrifuged if necessary, and the peptide content in the supernatant measured by UV absorption at 280 nm prior to the assessment of the biological activity.

(c) Characterization of recombined peptide chains.

The recombination of the relaxin peptide chains was monitored by HPLC and radioimmunoassay using an antibody raised to native porcine relaxin A22B29 and I125 Bolton-Hunter labelled A22B29 tracer (16). The biological activity of the recombined products was assessed using the rat uterine contractility assay (18).

The biological activity of the synthetic relaxin peptides was tested in the rat uterine contractility assay (18).

Table 1 shows the actual combination yields (measured by bioassay) obtained for various combinations of the natural (N) and synthetic (S) A and B chains and various synthetic analogues. Column 3 shows the actual combination yields (based on the B chain). Column 4 shows the yields recalculated on the basis of 100% yield for the recombined natural A22 and B28 chains.

The following points are noted.

(i) The recombination yield for the synthetic A22 B28 chain is very much lower than that for the natural chain. This is attributed to a lack of homogeneity in the synthetic peptides.

(ii) Recombination yields for the synthetic peptides are increased by shortening the B chain to 25 residues and/or by replacement of certain residues in the B and/or A chains.

(iii) Biological activity is retained even when the A and B chains are substantially shortened at both termini.

TABLE 1

| A-Chain | B-Chain | Recombination Yield (by BIOASSAY) | |
|---|---|---|---|
| NA (1-22) | NB (1-28) | 25% | 100% |
| SA (1-22) | SB (1-28) | 0.7 | 3 |
| SA (1-22) | SB[GLU$^1$](1-28) | 2.1 | 8 |
| SA (1-22) | SB[acetyl GLU$^1$](1-28) | 2.1 | 8 |
| SA (1-22) | SB (1-25) | 5.0-7.0 | 24 |
| SNle$^2$A (1-22) | SB (1-28) | 1.5 | 6 |
| SNle$^2$A (1-22) | SB[GLU$^1$](1-28) | 2.5 | 10 |
| SNle$^2$A (1-22) | SB[acetyl GLU$^1$](1-28) | 1.6 | 6 |
| SNle$^2$A (1-22) | SB (1-25) | 4.0 | 16 |
| SA (1-22) | SB (1-28)NH$_2$ | 1.7 | 7 |
| SA (1-22) | SB (1-23)NH$_2$ | 0.8-2.0 | 6 |
| SA (1-22) | SB[N—acetyl](4-23)NH$_2$ | 2.4 | 10 |
| SA (4-22) | SB[acetyl GLU$^1$](1-28) | 1.0 | 4 |
| SA (4-22) | SB (1-25) | 2.4 | 10 |
| SA (4-22) | SB (1-23)NH$_2$ | 1.3 | 5 |
| SA (4-22) | SB[N—acetyl](4-23)NH$_2$ | 1.3 | 5 |

REFERENCES

1. Schwabe, C., Steinetz, B., Weiss, G., Setaloff, A., McDonald, J.K., O'Byrne, E., Hochman, J., Cabbiere, B. & Goldsmith, L. (1978) Recent Progr. Hormone Res. 34, 123-211.
2. Schwabe, C., McDonald, J. K. & Steinetz, B. G. (1976) Biochem. Biophys. Res. Commun. 70, 397-405.
3. Schwabe, C., McDonald, J. K. & Steinetz, B. G. (1977) Biochem. Biophys, Res. Commun. 75, 503-510.
4. James, R., Niall, H., Kwok, S. & Bryant-Greenwood, G. (1977) Nature 267, 544-546.
5. Schwabe, C. (1981) in Relaxin (Bryant-Greenwood, G. D., Niall, H. D. & Greenwood, F. C., eds.), Elsevier-North Holland, New York.
6. Niall, H. D., John, M., James, R., Kwok, S., Mercado, R., Bryant-Greenwood, G., Bradshaw, R. A., Gast. M. & Biome, I. (1980) in Insulin, Chemistry Structure and Function of Insulin and Related Hormones (Brandenburg, D. & Wollmer, A., eds.), pp.719-725, Walter de Gruyter & Co., New York.
7. John, M. J., Borjesson, B. W., Walsh, J. R. & Niall, H. D. (1981) Endocrinology 198, 726-729.
8. Hudson, P., Haley, J., Cronk, M., Shine, J. & Niall, H. (1981) Nature 291, 127-131.
9. Gowan, L. K., Reinig, J. W., Schwabe, C., Bedarkar, S. & Blundell, T. L. (1981) FEBS Lett. 129, 80-82.
10. Bedarkar, S., Turnell, W. G., Blundell, T. L. & Schwabe, C. (1977) Nature 270, 449-451.

11. Isaacs, N., James, R., Niall, H., Bryant-Greenwood, G., Dobson, G., Evans, A. & North, A.C.T. (1978) Nature 271, 278–281.
12. Schwabe, C. & Harmon, S. J. (1978) Biochem. Biophys. Res. Commun. 84, 374–380.
13. Rawitch, A. B., Moore, W. V. & Frieden, E. H. (1980) Int. J. Biochem. 11, 357–362.
14. Sherwood, C. D. & O'Byrne, E. M. (1974) Arch. Biochem. Biophys. 160, 185–196.
15. Walsh, J. R. & Niall, H. D. (1980) Endocrinology 107, 1258–1260.
16. Tregear, C. W., Du, Y.-C., Kemp, B., Borjesson, B. W., Scanlon, D. & Niall, H. (1981) in Relaxin (Bryant-Greenwood), G. D., Niall, H. D. & Greenwood, F. C., eds.), pp. 151–164, Elsevier-North Holland, New York.
17. Du, Y.-C. Jiang, R-Q. & Tsou, C-L. (1965) Scientia Sinica 14, 229–236.
18 Wiquist, N. & Paul, K. G. (1958) Acta Endocrinol. 29, 135–146.
19. Greenfield, N. & Fasman, G. D. (1969) Biochemistry 8, 4108–4116.
20. Du, Y.-C., Zhang, Y.-S., Lu, Z.-X. & Tsou, C.-L. (1961) Scientia Sinica 10, 84–104.
21. Leach, S. J., Evans, D. J., Minasian, E., Sikaris, K. & Swayer, W. H. (1981) 7th American Peptide Symposium (in press).
22. Tam, J. P., Kent, S. B. H., Wong, T. W. and Merrifield, R. B. (1979) Synthesis 577–579.
23. Du, Y.-C. and Tsou, C. L. (1962) Atca Biochimica et Biophysica Sinica 2, 100–110.
24. Jiang, R. Q. Du, Y.-C. and Tsou, C. L. (1963) Acta Biochimica et Biophysica Sinica 3, 176–180.
25. Du, Y.-C., Minasian, E., Tregear, G. W. and Leach, S. J. (1982) Intern. J. Peptide and Protein Res.

We claim:

1. A synthetic porcine relaxin analogue selected from the group consisting of synthetic porcine relaxin analogues consisting of one of the following combinations of peptide chains: A (1-22) and B[GLU$^1$](1-28); A (1-22) and B[acetyl GLU$^1$](1-28); A (1-22) and B (1-25); Nle$^2$A (1-22) and B[GLU$^1$](1-28); SNle$^2$A (1-22) and B[acetyl GLU$^1$](1-28); Nle$^2$A (1-22) and B (1-25); A (1-22) and B (1-28)NH$_2$; A (1-22) and B (1-23)NH$_2$; A (1-22) and B[N-acetyl](4-23)NH$_2$; A (4-22) and B[acetyl GLU$^1$](1-28); A (4-22) and B (1-25); S (4-22) and B (1-23)NH$_2$; and A (4-22) and B[N-acetyl](4-23)NH$_2$.

2. A synthetic porcine relaxin analog according to claim 1, consisting of the A (1-22) and B[GLU$^1$](1-28) peptide chains.

3. A synthetic porcine relaxin analog according to claim 1, consisting of the A (1-22) and B [acetyl GLU$^1$](1-28) peptide chains.

4. A synthetic porcine relaxin analog according to claim 1, consisting of the Nle$^2$A (1-22) and B[GLU$^1$](1-28) peptide chains.

5. A synthetic porcine relaxin analog according to claim 1, consisting of the SNle$^2$A(1-22) and B[acetyl GLU$^1$](1-28) peptide chains.

6. A synthetic porcine relaxin analog according to claim 1, consisting of the Nle$^2$A (1-22) and B (1-25) peptide chains.

7. A synthetic porcine relaxin analog according to claim 1, consisting of the A (1-22) and B (1-28)NH$_2$ peptide chains.

8. A synthetic porcine relaxin analog according to claim 1, consisting of the A (1-22) and B (1-23)NH$_2$ peptide chains.

9. A synthetic porcine relaxin analog according to claim 1, consisting of the A (1-22) and B[N-acetyl](4-23)NH$_2$ peptide chains.

10. A synthetic porcine relaxin analog according to claim 1, consisting of the A (4-22) and B[acetyl GLU$^1$](1-28) peptide chains.

11. A synthetic porcine relaxin analog according to claim 1, consisting of the A (4-22) and B (1-25) peptide chains.

12. A synthetic porcine relaxin analog according to claim 1, consisting of the S (4-22) and B (1-23)NH$_2$ peptide chains.

13. A synthetic porcine relaxin analog according to claim 1, consisting of the A (4-22) and B[N-acetyl](4-23)NH$_2$.

14. A synthetic porcine relaxin analogue consisting of the A(1-22) and B(1-25) peptide chains.

15. A method for the synthesis of porcine relaxin or modified peptide forms or analogues thereof having relaxin-like activity, which comprises the steps of reducing a mixed solution of the S-sulfonated A and B peptide chains, or modified forms or analogues thereof; precipitating the reduced peptides with acetone; washing the mixed peptides; oxidizing the mixed peptides in solution in the presence of aqueous sodium chloride; and isolating the relaxin thus produced.

16. A method as claimed in claim 15, which comprises the steps of:
separately preparing or isolating the S-sulfonated A and B peptide chains;
forming a mixture of the S-sulfonated A and B peptides;
reducing the mixture at pH of about 7 to about 9 under nitrogen for at least 6 minutes;
adjusting the pH of the reduced mixture to 4.5 to 5.5 with acetic acid;
adding acetone to the mixture to precipitate the mixed peptides;
washing the mixed peptides with a suitable solvent, to remove the reducing agent;
oxidizing the mixed peptides at a pH of about 9.5 to about 11 for about 48 to 72 hours at a temperature of about 0° to 10° C. in the presence of sodium chloride in a concentration of at least about 0.1 M.

17. A method as claimed in claim 15, wherein a shortened form of one or both of the A and B chains is used.

18. A method as claimed in claim 15, wherein at least one amino-acid in one or both of the A and B chains is chemically modified prior to combination.

19. A method as claimed in claim 18, wherein the chemical modification comprises the addition of a protective group to a free amino group, and the protective group is optionally removed following combination.

20. A method as claimed in claim 17 wherein up to the first three amino acids of the A and/or B chains are omitted and/or up to the last five amino acids of the B chain are omitted.

21. A method as claimed in claim 18 wherein the chemical modification comprises the addition of a protective group and/or replacement of one or more of the natural amino acids in the A and/or B chains with a different amino acid.

22. A method as claimed in claim 21 wherein the protected group is formed by acetylation of a free amino group, amidation of C-terminal group or formation of an ester of a hydroxyl or carboxylic group.

23. A method as a claimed in claim 21 wherein Trp is replaced with Gly, Pca is replaced with Gln or Glu or Met is replaced with Nle.

* * * * *

UNITED STATES PATENT AND TRADEMARK OFFICE
CERTIFICATE OF CORRECTION

PATENT NO. : 4,656,249
DATED : April 7, 1987
INVENTOR(S) : Tregear et al

It is certified that error appears in the above-identified patent and that said Letters Patent is hereby corrected as shown below:

IN THE SPECIFICATION:

Column 8, lines 27, 28, 29, and 30, change "$Nle^2A$" to --$A[Nle^2]$--.

IN THE CLAIMS:

Claim 1, lines 5 and 7; Claim 4, line 2; and Claim 6, line 2; change "$Nle^2A$" to --$A[Nle^2]$--.

Claim 1, line 6 and Claim 5, line 2, change "$SNle^2A$" to --$A[Nle^2]$--.

Claim 1, line 10 and Claim 12, line 2, delete "S" and substitute therefore --A--.

Signed and Sealed this

Thirteenth Day of October, 1987

Attest:

DONALD J. QUIGG

Attesting Officer

Commissioner of Patents and Trademarks